United States Patent [19]

Bounous et al.

[11] Patent Number: 5,456,924

[45] Date of Patent: * Oct. 10, 1995

[54] METHOD OF TREATMENT OF HIV-SEROPOSITIVE INDIVIDUALS WITH DIETARY WHEY PROTEINS

[75] Inventors: Gustavo Bounous, Montreal; Phil Gold, Westmount, both of Canada

[73] Assignee: Immunotec Research Corporation Ltd., Montreal, Canada

[*] Notice: The portion of the term of this patent subsequent to Jul. 27, 2010 has been disclaimed.

[21] Appl. No.: 866,756

[22] Filed: Apr. 10, 1992

Related U.S. Application Data

[63] Continuation-in-part of Ser. No. 563,794, Aug. 3, 1990, Pat. No. 5,230,902, which is a continuation of Ser. No. 289,971, Dec. 23, 1988, abandoned, and a continuation-in-part of Ser. No. 417,246, Oct. 4, 1989, Pat. No. 5,290,511, which is a continuation-in-part of Ser. No. 289,971, Dec. 23, 1988, abandoned, which is a continuation-in-part of Ser. No. 188,271, Apr. 28, 1988, abandoned.

[51] Int. Cl.$^6$ ..................................................... A61K 35/20
[52] U.S. Cl. ................................ 424/535; 514/2; 514/21; 426/72
[58] Field of Search ......................... 514/2, 21; 530/365, 530/833; 424/535; 426/72

[56] References Cited

U.S. PATENT DOCUMENTS

| | | | |
|---|---|---|---|
| 4,880,626 | 11/1989 | McMichael | 424/88 |
| 4,983,387 | 1/1991 | Goldstein et al. | 424/88 |
| 5,030,449 | 7/1991 | Berzofsky et al. | 424/88 |
| 5,112,373 | 6/1992 | Eibl et al. | 424/85.8 |

FOREIGN PATENT DOCUMENTS

| | | | |
|---|---|---|---|
| 858533 | 12/1970 | Canada | 195/76 |
| 1263329 | 11/1989 | Canada | 195/128.3 |
| 2007258 | 7/1990 | Canada | 530/17.1 |
| 2011299 | 9/1990 | Canada | 167/140 |
| 2032653 | 12/1990 | Canada . | |
| 2022394 | 2/1991 | Canada | 530/7.06 |
| 2033347 | 5/1992 | Canada . | |
| 0339656 | 11/1989 | European Pat. Off. . | |
| 0374390 | 6/1990 | European Pat. Off. . | |
| 8910139 | 11/1989 | WIPO . | |

OTHER PUBLICATIONS

Bounous, G., Kongshavn, P., Gold, P., *Clinical and Investigative Medicine*, vol. 11, No. 4, pp. 271–278 (Aug. 1988).
Bounous, G., Batist, G., Gold, P., *Clinical and Investigative Medicine*, vol. 12, No. 3, pp. 154–161 (1989).
Fidelus, R. K., Tsan, M. F., *Cellular Immunol.*, vol. 97, pp. 155–163 (1986).
Gougerot-Pocidalo, M. A., et al., *Immunology*, vol. 64, pp. 281–288 (1988).
Noelle, R. J., Lawrence, D. A., *Biochem. J.*, vol. 198, pp. 571–579 (1981).
Anderson, M. E., Meister, A., *Proc. Natl. Acad. Sci.–USA*, vol. 80, pp. 707–711, (1983).
Meister, A., in Stranbury, J. B., eds, *Metabolic Basis of Inherited Diseases* 4th Edn. McGraw Hill, pp. 328–335 (1978).
Bounous, G., Gold, P., *Clinical and Investigative Medicine*, vol. 14, pp. 296–309 (1991).
Hirai, Y., et al., *Evaluation of the Immunological Enhancement Activities of Immunocol* (Dec. 13, 1990) Osaka, Japan.
Buhl, R., et al., *Lancet*, pp. 1294–1297 (Dec. 2, 1989).
Anderson, M. E., *C.R.C. Handbook of Methods for Oxygen Radical Research*, pp. 317–329 (1985).
Biological Abstracts, vol. 41, Abstract No. 84485, Voss et al. (Jun. 1991).
Biological Abstracts, vol. 41, Abstract No. 84488, Glauser et al. (Jun. 1991).

*Primary Examiner*—David M. Naff
*Assistant Examiner*—Jean C. Witz
*Attorney, Agent, or Firm*—John P. White

[57] ABSTRACT

Undenatured whey protein concentrate is administered to HIV-seropositive individuals to elevate their blood mononuclear cells, glutathione (GSH) level, body weight and sense of well being. In addition T-helper cells concentration and their T-helper cells/T-suppressor cells ratio are slightly elevated.

8 Claims, No Drawings

METHOD OF TREATMENT OF HIV-SEROPOSITIVE INDIVIDUALS WITH DIETARY WHEY PROTEINS

RELATED APPLICATIONS

This application is a continuation-in-part of U.S. application Ser. No. 563,794, filed Aug. 3, 1990, now U.S. Pat. No. 5,230,902, which is a continuation of U.S. Ser. No. 289,971, filed Dec. 23, 1988, now abandoned and a continuation-in-part of 417,246, now U.S. Pat. No. 5,290,571, filed on Oct. 4, 1989, which is a continuation-in-part of Ser. No. 289,971, now abandoned, which in turn is a continuation-in-part of U. S. Serial No. 188,271, filed Apr. 28, 1988, now abandoned, all of which are incorporated by reference herein.

BACKGROUND

Reference is made to twelve articles listed at the end of this specification, the contents of which are incorporated by reference herein.

Our studies showed that the humoral immune response (number of plaque-forming cells formed in response to sheep red blood cells) is significantly higher in mice fed a 20 g whey protein concentrate/100 g diet than in mice fed formula diets of similar nutritional efficiency containing 20 g/100 diet of any other type of commercially available semipurified food protein, such as casein, soy, wheat, corn, egg white, fish, beef protein, *Spirulina maxima, Scenedesmus algae* protein, or Purina mouse chow [1].

We have further shown that the immunoenhancing activity of dietary whey protein concentrate (WPC) is related to greater production of splenic glutathione (GSH) in the whey protein-fed animals during the oxygen-requiring antigen-driven clonal expansion of the lymphocyte [2]. It was then theorized that this might reflect the ability of the lymphocytes of whey protein diet-fed mice to offset potential oxidative damage, thus responding more fully to the antigenic challenge [3,4]. In fact, the capacity of a cell to recover from an oxidative insult is considered to be represented by its ability to regenerate intracellular stores of glutathione [5].

Our studies also showed that administration of S-(n-butyl) homocysteine sulfoximine, which reduces splenic glutathione in half, significantly reduced the humoral immune response of whey protein-fed mice. This was taken as further evidence for the important role of glutathione in the immunoenhancing effect of dietary whey protein [2].

Tissue glutathione concentration may be increased by administration of gamma-glutamyl-cysteine. Glutathione increased in the kidney by about 50%, 40–60 minutes after subcutaneous (s.c.) injection in mice, returning to control values 2 hours later [6]. The administered gamma-glutamyl-cysteine is transported intact and serves as a substrate for glutathione synthetase [7].

Advances in amino acid sequencing of food proteins allowed us to investigate the occurrence of glutamylcysteine groups in whey protein and the possible relation to glutathione promotion. Indeed, whey protein concentrate from bovine milk contains substantial amounts of glutamylcysteine groups, unlike casein, which does not increase tissue glutathione when fed to mice [1]. The glutamylcysteine groups are located primarily in the serum albumin fraction (six groups/molecule). Glutamylcysteine groups are extremely rare in animal and plant edible proteins. Extensive search of all available data on amino acid sequencing of edible proteins reveals that the Gly-Cys group with a disulfide link is indeed limited to some of the whey protein, and to the ovomucoid fraction of egg white which contains 2 of these groups in a 30,000 mol.wt.molecule [8].

Our recent [8] data further indicate that the humoral immune response is highest in mice fed a dietary whey protein concentrate exhibiting the highest solubility (unclenatured conformation) and, more importantly, a greater relative concentration of the thermolabile bovine serum albumin ($\geq 10\%$) and immunoglobulins. In addition, the mice fed this type of whey protein concentrate exhibit higher levels of tissue glutathione. The presence in the serum albumin fraction of glutamylcysteine groups (rare in food protein.) and the specific intramolecular bond as related to the undenatured conformation of the molecule are considered to be key factors in the glutathione-promoting activity of the protein mixture.

Recent experiments in Japan [9] showed that spleen cells of BALB/c male mice fed 25 g of our undenatured whey protein concentrate (WPC) (which we call "Immunocal") per 100 g diet for 4 weeks had an increased immune response to SRBC in vitro and a higher content of L3T4$^+$ cells ($12.58 \times 10^6 \pm 0.50$) than mice fed an isocaloric diet with 25 g. pure casein/100 g. diet ($3.69 \times 10^6 \pm 0.50$). Similarly, the spleen L3T4$^+$/LYt–2$^+$ ratio was $1.36 \pm 0.07$ in undenatured WPC fed mice and $0.55 \pm 0.07$ in casein-fed controls (P<0,001).

Materials and Methods

The whey protein concentrate (WPC) used in the examples was in undenatured form prepared from milk treated in the most lenient way compatible with accepted standards of safety with regard to bacterial contamination. The extremely high solubility index indicates that the proteins present are essentially undenatured, hence demonstrating the lineancy of the ultrafiltration process [8]. Although the proteins contained in the concentrates from the other commercially available sources examined were mostly in undenatured form, as indicated by the relatively high solubility of the concentrates, the content of serum albumin and immunoglobulins in these mixtures is below the level apparently necessary to produce a significant biological activity [8]. These very thermolabile proteins are denatured, hence precipitated and partially lost from whey when high pasteurization temperatures are utilized. Conversely, the relatively high concentrations of the thermosensitive serum albumin and immunoglobulins resulting from the low degree of pasteurization of milk in our WPC, may reflect more closely the pattern of raw milk. These data lend support to the hypothesis that the thermolabile Gly-Cys containing proteins such as serum albumin in undenatured conformation are crucial elements for the biological activity of whey protein concentrate.

The bovine whey protein concentrate (WPC) was especially prepared by the "Service de recherche sur les aliments du Ministers de l'agriculture du Quebec" in St-Hyacinthe, Quebec, Canada, with the following characteristics: pure protein content 75% (the rest mostly lactose, some fat and moisture); solubility index: (ph 4.6); 99.5%. Protein composition as % of total whey protein measured by polyacrylamide gel electrophoresis [8] was: beta-lactoglobulin $59.1 \pm 4.0$; alpha-lactalbumin:$6.6 \pm 0.7$; serum albumin: $9.7 \pm 1.0$; immunoglobulin $24.6 \pm 2.6$ (mean $\pm$SD). The solubility index should preferably be above 99%.

The serum albumin of about 10% of the total whey protein was almost twice the corresponding value found in other commercially available whey protein concentrates that have been examined. It is believed that a serum albumin level $\geq 10\%$ is highly advantageous to improving the immune system.

Serum albumin includes a substantial amount of glutamyl cystsine which is a substrate for glutathione synthesis in the body. The role of glutathione is discussed in detail in "The Biological Activity of Undenatured Dietary Whey Proteins: Role of Glutathione", *Clin. Invest Med* 14: 296–309, 1991, which is incorporated by reference in its entirety.

Immunoglobulin in the range of about 25 to 30% of total whey protein is also important. Pasteurization at 72° C. for 13 seconds resulted in an immunoglobulin level of 28±2%. We have found it possible to achieve a serum albumin level as high as 14±1% with milk pasteurized at 72% for 13 seconds.

Upon bacteriological analysis no staph, salmonella, B cereus, or E coli were isolated in either the WPC prepared by the "Service de recherche sur les Aliments due Ministers de l'agriculture du Quebec" or in the sample pasteurized at 72° C. for 13 seconds.

The method used to prepare the WPC used in the examples is schematically described below in Table 1.

TABLE 1

SCHEMATIC REPRESENTATION OF THE PROCESS TO PRODUCE OUR UNDENATURED WPC PRODUCT

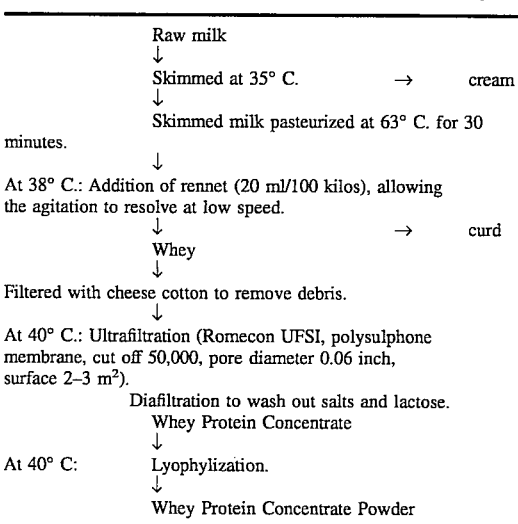

30 ml of heparinized blood are used to determine the glutathione content of blood mononucleated cells. Counted mononuclear cells are resuspended in phosphate buffered saline adjusted so that there are $10^7$ cells per tube. After centrifugation 900 μl of water is added to the pellet to lyse all the cells. To each aliquot is added 30% sulfosalicylic acid for a final concentration of 3% in i ml. After 15 minutes incubation, the samples are centrifuged, and the clear supernatant is used for the biochemical assay according to the method of Anderson [11]. Values are expressed as nanomol (nMol) of $GSH/10^7$ cells. Blood lymphocyte subsets are determined by flow-cytometry.

The total serum protein, including the albumins and the immunoglobulins is determined by the Biuret method. The level of Immunoglobulin A (IgA), Immunoglobulin G (IgG) and Immunoglobulin M (IgM) are measured by immunonephlometry.

DESCRIPTION OF THE INVENTION AND EXAMPLES

There are two important subsets of lymphocytes in the blood; (1) CD4, also called T-helper cells, because they help in the immune response and (2) CD8, also called T-suppressors because they have the opposite effect, i.e. they suppress the immune response. In HIV-seropositive individuals the number of CD4 (helper) cells is low, i.e. the ratio CD4/CD8 is down.

The object of this invention is to elevate the ratio of T helper cells to T suppressor cells. This is accomplished by the administration of undenatured whey protein concentrate.

The amount administered should be in the range of about 8 to 40 grams daily and preferably 20 to 40 grams daily. It is particularly beneficial to the glutathione level to administer 30 to 40 grams daily.

As more fully described in U.S. application Ser. No. 563,794 filed Aug. 3, 1990, which is incorporated in its entirety by reference, raising the glutathione level is beneficial to the immune system.

EXAMPLE 1

A whey protein concentrate as previously described was administered to 3 male HIV-seropositive individuals identified in Table 2 as A, B and C. The product was drunk cold daily in a liquid chosen by the patient. Originally a fourth patient D was included but he took the WPC sporadically for lack of discipline and none during the final days of the study. He therefore has been classified in Table 2 as a control the other controls are E and F.

The daily intake of WPC was increased stepwise. During the first three weeks 8.4 grams were prescribed daily, in the following three weeks 19.6 g, in the next three weeks 28 grams, and 39.2 grams in the final three weeks.

The observations made are shown below in Table 2.

TABLE 2

| Patient Initials (age) | Weeks on Whey | Energy (K Cal) Protein g (1) | Ideal Body Weight (Kg) | Body Weight (Kg) | CD4 % (2) | Helper Absolute (3) | CD4/CD8 (4) | GSH n mol–$10^2$ cells (5) | Total | Serum Alb | Proteins IgG | in IgA | % IgM |
|---|---|---|---|---|---|---|---|---|---|---|---|---|---|
| | | | | | | WHEY | | | | | | | |
| A (35) | 0 | 2180 / 87 | 86 | 102.5 | 23 | 368 | 0.38 | 9.75 | 77 | 42 | 20.8 | 1.54 | 1.14 |
| | 6 | 1800 | | 105 | 26 | 546 | 0.45 | 10.34 | 74 | 39 | 19.4 | 1.56 | 1.16 |

TABLE 2-continued

| Patient Initials (age) | Weeks on Whey | Energy (K Cal) / Protein g (1) | Ideal Body Weight (Kg) | Body Weight (Kg) | CD4 % (2) | Helper Absolute (3) | CD4/CD8 (4) | GSH n mol–10² cells (5) | Total | Serum Alb | Proteins IgG | in IgA | % IgM |
|---|---|---|---|---|---|---|---|---|---|---|---|---|---|
| | 12 | 106 / 2111 | | 108 | 24 | 480 | 0.41 | 13.9 | 80 | 42 | 20.1 | 1.61 | 1.05 |
| B (32) | 0 | 100 / 1870 | 75.2 | 73.9 | 15 | 435 | 0.22 | 10.22 | 82 | 50 | 12.3 | 4.38 | 0.75 |
| | 6 | 84 / 2035 | | 74.5 | 19 | 532 | 0.28 | 9.6 | 79 | 45 | 14.3 | 4.53 | 0.76 |
| | 12 | 140 / 2100 | | 76 | 17 | 442 | 0.24 | 17.04 | 72 | 50 | 16.9 | 5.81 | 0.95 |
| C (20) | 0 | 138 / 2400 | 78 | 76 | 24 | 672 | 0.39 | 10.38 | 82 | 52 | 12.4 | 3.59 | 0.76 |
| | 6 | 100 / 2200 | | 77.5 | 27 | 864 | 0.46 | 12.55 | 81 | 49 | 12.9 | 3.99 | 0.58 |
| | 12 | 116 / 1400 | | 78 | 26 | 676 | 0.45 | 7.06 | 80 | 50 | 12.8 | 3.8 | 0.7 |
| CONTROL | | | | | | | | | | | | | |
| D | 0 | 98 / 2940 | | 95.5 | 27 | 540 | 0.47 | 12.36 | 75 | 47 | 15.6 | 1.63 | 1.34 |
| | 6 | 107 / 2500 | | 85 | 25 | 650 | 0.42 | 8.59 | 73 | 42 | 15 | 1.5 | 1.19 |
| E (38) | 0 | 118 / 2500 | 70 | 69.5 | 17 | 420 | | 10.3 | 81 | 44 | | | |
| | 6 | 98 / 2600 | | 68.5 | 21 | 371 | | 11 | 82 | 44 | | | |
| | 12 | 130 / 2480 | | 68 | 18 | 359 | | 9.8 | 81 | 44 | | | |
| F (37) | 0 | 108 / 2200 | 74 | 74 | 16 | 263 | | 11.08 | 80 | 43 | | | |
| | 6 | 108 / 2100 | | 73 | 12 | 222 | | 10.3 | 83 | 43 | | | |
| | 12 | 120 / 2300 | | 72 | 12.5 | 230 | | 9 | 80 | 42 | | | |
| | | 110 | | | | | | | | | | | |

(1) The energy and protein intake indicated represents the mean value for the preceding weeks.
(2) Normal range: 35–55
(3) Normal range: 580–1250
(4) Normal range: 1.42–3.56
(5) GSH: Glutathione content of mononuclear blood cells. Normal value in healthy HIV seronegative individual of corresponding age: $17.05 \pm 2.40$ (mean $\pm$ SD)

In Table 2:

CD 4% means the percentage of $CD_4$ (helper cells) of the total lymphocytes in the blood.

Helper absolute refers to the real number of CD4 cells per unit of blood ($\times 10^3$ per microliter (µl))

CD4/CD8 refers to the ratio of the two types of lymphocytes in the blood, i.e. the T-helper cells and the T-suppressor cells.

Total refers to the total amount of protein in the serum which includes the albumins and the imunoglobulins.

IgA means Immunoglobulin A

IgG means Immunoglobulin G

IgM means Immunoglobulin M

The data in Table 2 and other information gathered during the course of the work indicates the following.

Three patients took the undenatured WPC daily for the 3-month period without any adverse side effects. In all these patients body weight increased progressively (from 2 to 7 kilos); and in fact two of them (C and B) reached ideal body weight. Serum proteins, including albumin, remained unchanged and within normal range, indicating that protein replenishment per se was not likely the cause of increased body weight.

In all three of these patients the blood T-helper cells concentration and the T-helper/suppressor ratios were moderately but consistently higher during the study than before undenatured WPC administration.

The blood mononuclear cells glutathione content was, as expected [10], below normal values in all patients at the onset of the study. Over the three-month period, however, glutathione levels increased and in one case (B) rose by 70% to reach normal value.

Systemic glutathione deficiency in symptom-free HIV-seropositive individuals [10] at page 1297 presents the re-establishment of normal extracellular concentrations of glutathione as an unsolved problem, because GSH administered intravenously has a half life of only 1–6 minutes. This problem is however solved in accordance with this invention by the administration of undenatured WPC.

These objective changes were accompanied by a markedly improved sense of well being in all three patients.

It is noteworthy that one patient over-concerned that the beneficial increase in body weight could hamper his lean appearance, drastically reduced energy and undenatured WPC intake during the second period of study. (C, Table 2). During this time body weight increase was reduced, and glutathione and T-helper cells failed to rise.

As indicated earlier, patient D. considered as control for his total lack of submission to the protocol, exhibited a drop in body weight, T-helper/suppressor ratio and glutathione on the 6-week end point and did not show up for the 12-week appointment. The other two controls (E. and F.) exhibited weight loss and no change in GSH levels.

The example indicates that whenever patients essentially maintained their energy intake at pre-study levels with only minor reductions in the prescribed WPC intake, body weight increased and specific HIV indicators such as a blood cell glutathione, T-helper cells concentrations and T-helper/suppressor ratios were all moderately higher during the WPC administration.

The positive effects of undenatured WPC observed in this very limited number of HIV-seropositive individuals acquires significance if viewed on the background of a large number of animal experiments showing increased cellular GSH and immune response by our WPC [1,2,8,9]. Animal studies emphasize the fact that the immunoenhancing effect of undenatured WPC is not related to a greater systemic nutritional efficiency, when compared to several other protein sources with similar nutritional efficiency but no significant biological activity. Mice fed undenatured WPC did not exhibit increased body growth nor any changes in serum protein levels. Similarly in our patients undenatured WPC did not produce any change in serum proteins which remained constant throughout the study. The increase in body weight observed in our patients did not correlate with increase in energy or protein intake throughout the study period but rather with improved sense of well being and HIV specific blood parameters. The extra protein intake through the undenatured WPC was generally compensated by reduced intake of protein from other sources.

The presence of glutamylcysteine groups in the serum albumin component of the whey protein concentrate is considered to be a key factor in the glutathione-promoting and immunoenhancing activity of the protein mixture of the undenatured WPC. Our laboratory studies indicate that whey protein concentrates from other sources, did not produce significant biological activities while exhibiting similar nutritional efficiency. The percent serum albumin concentration in these products is (as mean ±SD) respectively: 4±1 in Promod (Ross Laboratories), 4± in Alacen 855 (New Zealand Dairy), 4.8± in Lacprodan −80 (produced from 1989 by Danmark Protein), 4.8±0.1 in Sapro (Saputo, Montreal), 4±1 in Savorpro −75 (Golden Cheese, CA), 5±1 in Bioisolate (Lesueur Isolates, Minneapolis) [8] and 4.3±1 in Promix (Dumex, Quebec). Similarly, the content of the other thermolabile protein, immunoglobulin, was about half the value of the undenatured WPC used in this study).

The results indicate that undenatured whey proteins by providing specific fuel for glutathione replenishment in the immunocytes could represent an adjuvant to other forms of therapy.

Historically, and up until now, bacteria and spores in milk were reduced by thermal treatment (pasteurization). In order to be effective, that method inevitably produced denaturation, and hence subsequent precipitation and loss in the curd of a substantial amount of the most thermolabile and presumed biologically active fractions of serum albumin and immunoglobulin.

Our objective is to obtain a whey protein concentrate (w.p.c) containing the proteins in proportion and conformation as close as possible to that of raw milk, compatible with accepted safety standards of bacterial content. Up until now we have utilized the lowest acceptable level of heat treatment of milk in order to preserve thermolabile whey protein. From now on we will achieve this objective with a new method based on membrane microfiltration.

Utilizing Bactocatch (Alfa-Laval Ltd. Scarborough, Ontario) we can obtain by special membrane microfiltration of the skim milk a permeate whose bacteria content has been reduced to less than 0.5% of original input levels.

This permeate is then treated with rennet and the proteins in the whey supernatant concentrated by a lenient procedure to obtain the desired undenatured whey protein concentrate. We believe that the membrane microfiltration concept replacing heat treatment of milk will provide in the future the appropriate way to preserve heat labile whey proteins, although techniques and equipment may be improved in time.

REFERENCES

1) Bounous G, Kongshavn P. A. L, Gold. P: The immunoenhancing property of dietary whey protein concentrate. Clin Invest Med 11:271–8, 1988.
2) Bounous G, Batist G, Gold P: Immunoenhancing property of dietary whey protein in mice: Role of glutathione. Clin Invest Med 12:154–61, 1989.
3) Fidelus R. K., Tsan M. F.: Enhancement on intracellular glutathione promotes lymphocyte activation by mitogen. Cell Immunol 97: 155–63, 1986.
4) Gougerot-Pocidalo M. A., Fay M, Roche S: Mechanisms by which oxidative injury inhibits the proliferative response of human lymphocytes to PHA, Effect of the thiol compound 2-mercaptoethanol. Immunology 64: 281–8, 1988.
5) Noelle R. J., Lawrence D. A.: Determination of glutathione in lymphocytes and possible association of redox state and proliferative capacity of lymphocytes. Biochem J 198: 571–9, 1981.
6) Anderson M. E., Meister A: Transport and direct utilization of gamma-glutamylcyst(e)ine for glutathione synthesis. Proc Natl Acad Sci 80:707–11, 1983.
7) Meister A: 5-Oxoprolinuria and other disorders of glutathione biosynthesis. In:Stranbury J. B., Wymgaarden J. B., Frederikson D. S., eds. Metabolic basis of inherited diseases 4th edn. McGraw Hill, 1978:328–35
8) Bounous G, Gold P: The biological activity of undenatured dietary whey proteins: role of glutathione. Clin Invest Med 14:296–309, 1991.
9) Hirai Y, Nakay S, Kikuishi H, Kawai K; Report: Evaluation of the immunological enhancement activities of Immunocal. Otsuka Pharmaceutical Co. Ltd: Cellular Technology Institute: Dec. 13, 1990, Osaka, Japan.

10) Buhl R, Holroyd K. J., Mastrangeli A, Cantin A. M., Jaffe H. A., Wells C, Saltini C, Crystal R. G.:Systemic glutathione deficiency in symptom-free HIV-seropositive individuals. Lancet(December 2): 1294–7, 1989.

11) Anderson ME: Tissue glutathione: In:C.R.C. Handbook of methods for oxygen radical research. Boca Raton, Fla.:CRC Press, Inc., 1985:317–29

We claim:

1. A method of treating HIV-seropositive individuals so as to increase their blood mononuclear cell glutathione concentration and to maintain or increase body weight which comprises administering to HIV-seropositive individuals a substantially undenatured whey protein concentrate, wherein the substantially undenatured whey protein concentrate comprises substantially all the heat labile whey protein contained in raw milk, in an amount effective to increase their blood mononuclear cell glutathione concentration and maintain or increase body weight.

2. The method as in claim 1 in which the undenatured whey protein concentrate has a solubility index at pH 4.6 of 99%.

3. The method as in claim 1 in which the undenatured whey protein concentrate has a protein composition comprising beta-lactoglobulin 59.1±4.0, alpha lactalbumin 6.6±0.7, serum albumin 9.7±1.0, and immunoglobulin 24.6±2.6.

4. The method as in claim 1 in which the amount of undenatured whey protein concentrate administered daily is in the range of about 8 to 40 grams daily.

5. The method as in claim 4 in which the range is about 20 to 40 grams daily.

6. The method as in claim 5 in which the range is about 30 to 40 grams daily.

7. The method as in claim 2 in which the undenatured whey protein concentrate has a serum albumin level of at least about 9.5%.

8. The method as in claim 1 in which the substantially undenatured whey protein concentrate comprises substantially all the glutamyl-cysteine group containing proteins contained in raw milk.

* * * * *